United States Patent
Li et al.

(10) Patent No.: US 9,522,891 B2
(45) Date of Patent: Dec. 20, 2016

(54) PYRIDAZINE DERIVATIVES AND USE THEREOF AS MEDICAMENTS FOR TREATING MICRORNA VIRAL INFECTION

(71) Applicant: INSTITUTE OF PHARMACOLOGY AND TOXICOLOGY ACADEMY OF MILITARY MEDICAL SCIENCES P.L.A. China, Beijing (CN)

(72) Inventors: Song Li, Beijing (CN); Hongliang Wang, Beijing (CN); Junhai Xiao, Beijing (CN); Xian Zhang, Beijing (CN); Lili Wang, Beijing (CN); Zhibing Zheng, Beijing (CN); Wu Zhong, Beijing (CN); Yunde Xie, Beijing (CN); Xingzhou Li, Beijing (CN); Xinbo Zhou, Beijing (CN); Guoming Zhao, Beijing (CN); Xiaokui Wang, Beijing (CN)

(73) Assignee: INSTITUTE OF PHARMACOLOGY AND TOXICOLOGY ACADEMY OF MILITARY MEDICAL SCIENCES P.L.A. CHINA, Beijing (CN)

( * ) Notice: Subject to any disclaimer, the term of this patent is extended or adjusted under 35 U.S.C. 154(b) by 0 days.

(21) Appl. No.: 14/494,285

(22) Filed: Sep. 23, 2014

(65) Prior Publication Data

US 2015/0011558 A1   Jan. 8, 2015

Related U.S. Application Data

(62) Division of application No. 13/813,806, filed as application No. PCT/CN2011/077896 on Aug. 2, 2011, now Pat. No. 8,846,678.

(30) Foreign Application Priority Data

Aug. 2, 2010 (CN) .......................... 2010 1 0242472

(51) Int. Cl.
C07D 237/20 (2006.01)
(52) U.S. Cl.
CPC .................... *C07D 237/20* (2013.01)
(58) Field of Classification Search
CPC .................................................. C07D 237/20
See application file for complete search history.

(56) References Cited

U.S. PATENT DOCUMENTS 5,231,184 A  7/1993  Stokbroekx et al.

FOREIGN PATENT DOCUMENTS

| CN | 1033274 A   | 6/1989  |
|----|-------------|---------|
| CN | 1052857 A   | 7/1991  |
| EP | 0320032 A1  | 6/1989  |
| EP | 0435381 A1  | 7/1991  |
| WO | 00/78746 A1 | 12/2000 |

OTHER PUBLICATIONS

Linden et al. Replication and Inhibitors of Enteroviruses and Parechoviruses. Viruses. Aug. 10, 2015;7(8):4529-62.*
Wang Hongliang: "Pharmacophore-based design, synthesis, and biological evaluation of novel chloro-pyridazine piperazines as human rhinoviras (HRV-3) inhibitors"• Bioorganic & Medicinal Chemistry Letters vol. 21, Dec. 7, 2010, pp. 1057-1059.
Wang Hongliang: "3-Chloro-6-{4-[3-(4-chlorophenoxy)-propyl] piperazin-1-yl}pyridazine" Acta Crystallographica Section E: Structure Reports Online vol. E66, No. 3, Feb. 27, 2010, p. 0716.
International Search Report mailed Sep. 22, 2011 (PCT/CN2011/ 077896); ISA/CN.
Extended European Search Report mailed Dec. 4, 2013 (PCT/ CN2011077896).
Office Action issued in corresponding Chinese Application No. 201010242472.X dated Aug. 22, 2013.
Fan, Shi-Yong, et al. "Synthesis and Evaluation of Novel Chloropyridazine Derivatives as Potent Human Rhinovirus (HRV) Capsid-Binding Inhibitors," Bioorganic & Medicinal Chemistry 17 (2009) 621-624.
Hayden Frederick G. et al., "Safety and Efficacy of Intranasal Pirodavir (R77975) in Experimental Rhinovirus Infection," Antimicrobial Agents and Chemotherapy, vol. 6, No. 4., Apr. 1992, p. 727-732.

* cited by examiner

*Primary Examiner* — Brian McDowell
(74) *Attorney, Agent, or Firm* — Banner & Witcoff, Ltd.

(57) ABSTRACT

Disclosed are pyridazine derivatives represented by Formula I or pharmaceutically acceptable salts or hydrates thereof, pharmaceutical compositions comprising the compounds, methods of treating and/or preventing diseases or disorders associated with viral infections in patients using the compounds, and the use of the compounds in preparing the medicaments for treating and/or preventing diseases or disorders associated with viral infections. The compounds represented by Formula I have antiviral activity, especially anti-microRNA viral activity. Symbols in the compounds represented are described in the specification.

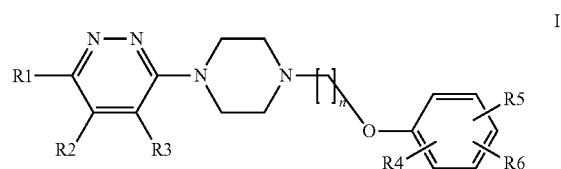

10 Claims, No Drawings

PYRIDAZINE DERIVATIVES AND USE THEREOF AS MEDICAMENTS FOR TREATING MICRORNA VIRAL INFECTION

The present application is a divisional application of U.S. patent application Ser. No. 13/813,806 filed Apr. 15, 2013, which is a U.S. National Phase filing of International Application No. PCT/CN2011/077896, filed Aug. 2, 2011, designating the United States of America and claiming priority to Chinese Patent Application No. 201010242472.X, filed Aug. 2, 2010. The present application claims priority to and the benefit of all the above-identified applications, and all the above-identified applications are incorporated by reference herein in their entireties.

TECHNICAL FIELD

The present invention relates to a substituted pyridazine derivative or a pharmaceutically acceptable salt or hydrate thereof, a pharmaceutical composition comprising the same, and use thereof as a medicament for combating picornavirus infections in the prevention and/or treatment of a viral disease caused by a picornavirus.

BACKGROUND ART

The Picornaviridae is the smallest animal RNA virus known in the art, and it has 7 genera, i.e., rhinovirus genus, enterovirus genus, aphthovirus genus, cardiovirus genus, hepatovirus genus, double ECHOviruses (enteric cytopathic human orphan viruses) genus, and some unclassified picornaviruses. Picornaviruses can induce diseases in many systems, such as respiratory diseases, hand-foot-mouth diseases, meningitis/encephalitis, acute poliomyelitis, cardiovascular diseases, hemorrhagic conjunctivitis, and hepatitis.

In the late 1980s, virology developed greatly. Several important events in viral life cycle have been well described, and many molecular targets are confirmed. In recent years, the appearance of many novel antiviral drugs also promotes the development of virology. The activities of picornavirus inhibitors are studying. These inhibitors act on targets including viral capsid protein 1 (VP1), a relatively conservative capsid structure for mediating viral absorption/uncoating process. VP1s of viruses of different serotypes are of highly conservative structure, but are very important for replication of viruses, and inhibitors acting on this target could be drugs for combating picornaviruses, among which Pirodavir is a typical representative (ANTIMICROBIAL AGENTS and CHEMOTHERAPY, 36(4), 727-732), and this compound exhibits significant activity against rhinovirus (HRV) in vivo and in vitro. Bioorg Med Chem. 2009, 17: 621-624 discloses a series of compounds with good inhibition activity to HRV, among which the compounds 4-{2-[N-(3-chloropyridazin-4-yl)piperidin-4-yl]ethoxyl}benzoic acid ethyl ester (5f) and 3,6-dichloro-4-{4-[2-(4-ethoxylphenoxy)ethyl]piperazin-1-yl}pyridazine (5c) have an activity comparable to Pirodavir, but have a relatively low toxicity, and a relatively high index of selectivity.

However, there is still need to develop an antiviral agent having a novel structure, effectiveness, and optionally one or more physiological and/or physicochemical advantages.

DESCRIPTION OF THE INVENTION

The object of the present invention is to discover and develop a novel small molecule compound acting on VP1 of a picornavirus, which can block the adhesion and uncoating of the virus, has an inhibition activity on a picornavirus, and thereby accomplishes the goals of the prevention and/or treatment of a disease caused by a picornavirus.

After extensive studies, the present inventors have found that a compound of the following Formula I can act on VP1 of picornavirus to block the adhesion and uncoating of the virus, and thus may be used for the prevention and/or treatment of a disease caused by a picornavirus. The present invention is thus accomplished on the basis of the above findings.

The first aspect of the present invention provides a compound of Formula I:

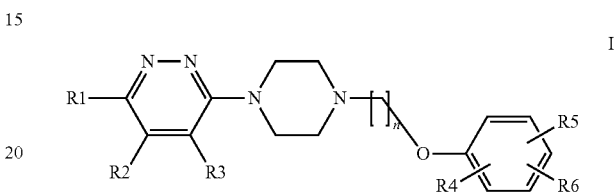

or a pharmaceutically acceptable salt or hydrate, in which:

R1, R2 and R3 are each independently selected from the group consisting of hydrogen and halogen (such as fluorine, chlorine, bromine or iodine, preferably fluorine or chlorine);

n is an integer of 2 to 5 (such as an integer of 3 to 5, an integer of 3 to 4, an integer of 2, 3, 4 or 5, preferably an integer of 3 to 5, an integer of 3 to 4, or 2, 3 or 4); and R4, R5 and R6 are each independently selected from the group consisting of hydrogen, halogen (such as fluorine, chlorine, bromine or iodine), a straight or branched C1-C8 alkyl (such as a straight or branched C1-C8 alkyl, a straight or branched C1-C6 alkyl, a straight or branched C1-C4 alkyl, methyl, ethyl, n-propyl, isopropyl, n-butyl or tert-butyl), —COOR7 and —OR8; wherein R7 and R8 are each independently selected from the group consisting of hydrogen, a straight or branched C1-C6 alkyl (such as a straight or branched C1-C4 alkyl, methyl, ethyl, n-propyl, isopropyl, n-butyl or tert-butyl).

The compound according to the first aspect of the present invention is a compound of Formula Ia:

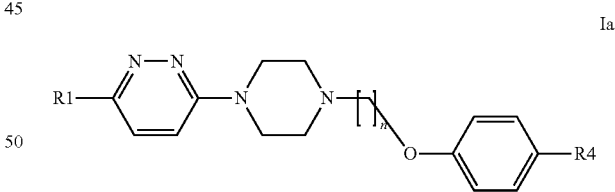

or a pharmaceutically acceptable salt or hydrate, wherein:

R1 is selected from the group consisting of hydrogen, fluorine, chlorine, bromine and iodine (preferably fluorine and chlorine);

n is an integer of 2 to 5 (such as an integer of 3 to 5, an integer of 3 to 4, an integer of 2, 3, 4 or 5, preferably an integer of 3 to 5, an integer of 3 to 4, or 2, 3 or 4); and R4 is selected from the group consisting of hydrogen, halogen (such as fluorine, chlorine, bromine, or iodine), a straight or branched C1-C8 alkyl (such as a straight or branched C1-C8 alkyl, a straight or branched C1-C6 alkyl, a straight or branched C1-C4 alkyl, methyl, ethyl, n-propyl, isopropyl, n-butyl or tert-butyl), —COOR7 and —OR8; wherein R7 and R8 are each independently selected from the group consisting of hydrogen, a straight or branched C1-C6 alkyl (such as a straight or branched C1-C4 alkyl, methyl, ethyl, n-propyl, isopropyl, n-butyl or tert-butyl).

The compound according to the first aspect of the present invention is a compound of Formula Ia:

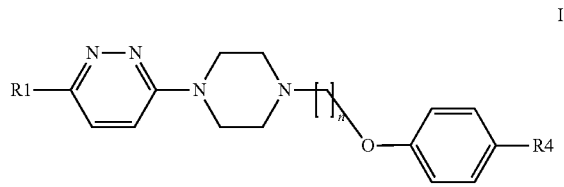

Ia or a pharmaceutically acceptable salt or hydrate, in which:

R1 is selected from the group consisting of fluorine and chlorine;

n is an integer of 3 to 5 (preferably an integer of 3 to 4, or 3 or 4); and

R4 is selected from the group consisting of halogen (such as fluorine, or chlorine), a straight or branched C1-C6 alkyl (such as a straight or branched C1-C4 alkyl, methyl, ethyl, n-propyl, isopropyl, n-butyl or tert-butyl), —COOR7 and —OR8; wherein R7 and R8 are each independently selected from the group consisting of hydrogen, a straight or branched C1-C4 alkyl (such as methyl, ethyl, n-propyl, isopropyl, n-butyl or tert-butyl).

The compound according to the first aspect of the present invention is a compound of Formula Ia:

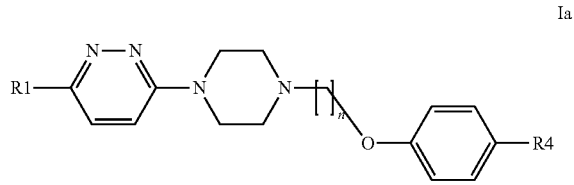

Ia or a pharmaceutically acceptable salt or hydrate, in which:

R1 is chlorine;

n is 3 or 4; and

R4 is selected from the group consisting of a straight or branched C1-C6 alkyl (such as a straight or branched C1-C4 alkyl, methyl, ethyl, n-propyl, isopropyl and n-butyl), —COOR7 and —OR8; wherein R7 and R8 are each independently selected from the group consisting of hydrogen and a straight or branched C1-C4 alkyl (such as methyl, ethyl, n-propyl, isopropyl and n-butyl).

The compound according to the first aspect of the present invention is selected from the group consisting of:

3-{4-[3-(4-ethoxylphenoxy)propyl]piperazin-1-yl}-6-chloropyridazine,

3-{4-[3-(4-methylphenoxy)propyl]piperazin-1-yl}-6-chloropyridazine,

3-{4-[3-(4-ethylphenoxy)propyl]piperazin-1-yl}-6-chloropyridazine,

3-{4-[3-(4-isopropylphenoxy)propyl]piperazin-1-yl}-6-chloropyridazine,

4-{3-[4-(6-chloropyridazin-3-yl)piperazin-1-yl]propoxy}benzoic acid methyl ester, and 4-{3-[4-(6-chloropyridazin-3-yl)piperazin-1-yl]propoxy}benzoic acid ethyl ester, or a pharmaceutically acceptable salt or hydrate.

The second aspect of the present invention provides a pharmaceutical composition comprising a therapeutically and/or preventively effective amount of the compound according to the first aspect of the present invention or a pharmaceutically acceptable salt or hydrate thereof, and optionally one or more pharmaceutically acceptable carrier or excipient.

The third aspect of the present invention provides use of the compound according to the first aspect of the present invention or a pharmaceutically acceptable salt or hydrate thereof, or the pharmaceutical composition according to the second aspect of the present invention in the manufacture of a medicament for treating and/or preventing a disease or disorder associated with viral infections. In one embodiment of the third aspect of the present invention, the virus is a picornavirus. In one embodiment of the third aspect of the present invention, the picornavirus is selected from the group consisting of: rhinoviruses, enteroviruses, aphthoviruses, cardioviruses, hepatoviruses, dual ECHOviruses. In one embodiment of the third aspect of the present invention, the disease or disorder associated with viral infections is selected from the group consisting of: respiration diseases (including but not being limited to: common cold (such as summer cold), pharyngitis, tonsillitis and croup), hand-foot-mouth diseases, meningitis/encephalitis, acute poliomyelitis, cardiovascular diseases, hemorrhagic conjunctivitis, and hepatitis.

The fourth aspect of the present invention provides use of the compound of the first aspect of the present invention or a pharmaceutically acceptable salt or hydrate thereof or the pharmaceutical composition of the second aspect of the present invention as a medicament for combating a disease or disorder associated with viral infections. In one embodiment of the fourth aspect of the present invention, the virus is a picornavirus. In one embodiment of the fourth aspect of the present invention, the picornavirus is selected from the group consisting of: rhinoviruses, enteroviruses, aphthoviruses, cardioviruses, hepatoviruses, dual ECHOviruses. In one embodiment of the fourth aspect of the present invention, the disease or disorder associated with viral infections is selected from the group consisting of: respiration diseases (including but not being limited to: common cold (such as summer cold), pharyngitis, tonsillitis and croup), hand-foot-mouth diseases, meningitis/encephalitis, acute poliomyelitis, cardiovascular diseases, hemorrhagic conjunctivitis, and hepatitis.

The fifth aspect of the present invention provides a method for treating and/or preventing a disease or disorder associated with viral infections in a subject in need thereof, comprising administering to the subject a therapeutically and/or preventively effective amount of the compound according to the first aspect of the present invention or a pharmaceutically acceptable salt or hydrate thereof, or the pharmaceutical composition of the second aspect of the present invention. In one embodiment of the fifth aspect of the present invention, the virus is a picornavirus. In one embodiment of the fifth aspect of the present invention, the picornavirus is selected from the group consisting of: rhinoviruses, enteroviruses, aphthoviruses, cardioviruses, hepatoviruses, dual ECHOviruses. In one embodiment of the fifth aspect of the present invention, the disease or disorder associated with viral infection is selected from the group consisting of: respiration diseases (including but not being limited to: common cold (such as summer cold), pharyngitis, tonsillitis and croup), hand-foot-mouth diseases, meningitis/encephalitis, acute poliomyelitis, cardiovascular diseases, hemorrhagic conjunctivitis, and hepatitis.

The sixth aspect of the present invention provides the compound according to the first aspect of the present invention or a pharmaceutically acceptable salt or hydrate thereof for treating and/or preventing a disease or disorder associated with viral infections. In one embodiment of the sixth aspect of the present invention, the virus is a picornavirus. In one embodiment of the sixth aspect of the present invention, the picornavirus is selected from the group consisting of: rhinoviruses, enteroviruses, aphthoviruses, cardioviruses, hepatoviruses, dual ECHOviruses. In one embodiment of the sixth aspect of the present invention, the disease or disorder associated with viral infection is selected from the group consisting of: respiration diseases (including but not being limited to: common cold (such as summer cold), pharyngitis, tonsillitis and croup), hand-foot-mouth diseases, meningitis/encephalitis, acute poliomyelitis, cardiovascular diseases, hemorrhagic conjunctivitis, and hepatitis.

The various aspects and features of the present invention are further described as follows.

All cited references are incorporated herein by their full texts, and if the meaning of an expression in these references is inconsistent with that in the present invention, the meaning of the expression in the present invention should be used. In addition, the terms and phrases used in the present invention have common meanings known by those skilled in the art, unless they are defined otherwise. If the meaning of a term or phrase defined in the present invention is inconsistent with that well known in the art, the meaning defined in the present invention should be used.

As used herein, by the term "pharmaceutically acceptable", for example, when used in "a pharmaceutically acceptable salt", it mans that the salt is not only physiologically acceptable in a subject, but also a substance having pharmaceutical value.

As used herein, the term "alkyl" comprises a straight and branched saturated hydrocarbonyl with the designated number of carbon atoms. As used herein, the term "$C_{1-6}$ alkyl" refers to an alkyl having the designated number of carbon atoms, which is a straight or branched alkyl, and may comprise its subgroups, such as $C_{1-4}$ alkyl, $C_{1-3}$ alkyl, $C_{1-2}$ alkyl, $C_{2-6}$ alkyl, $C_{2-4}$ alkyl, for example, methyl, ethyl, n-propyl, isopropyl, n-butyl, iso-butyl, tert-butyl, pentyl, or hexyl.

As used herein, the term "halogen", "halogen atom", "halogenated" represents fluorine, chlorine, bromine or iodine, especially fluorine, chlorine or bromine.

As used herein, the term "effective amount" refers to a dose that can achieve the treating and/or preventing of the disease or disorder as defined in the present invention in a subject.

As used herein, the term "pharmaceutical composition" refers to a "composition", which can achieve the treating and/or preventing of the disease or disorder as defined in the present invention in a subject, especially a mammal.

As used herein, the term "subject" may refer to a patient or an animal, especially human, dog, monkey, bovine, or equine, which is administered with the compound of Formula I of the present invention or a pharmaceutical composition thereof to treat and/or prevent the disease or disorder as defined in the present invention.

As used herein, "%" refers to a weight/weight percentage, especially in a situation of describing solid substance, unless it is specifically indicated otherwise. Of course, when it is described for a liquid substance, the "%" may refer to a weight/volume percentage (in the case of a solid being dissolved in a liquid), or a volume/volume percentage (in the case of a liquid being dissolved in a liquid).

One embodiment of the present invention relates to a method for the prevention and/or treatment of a disease associated with an infection caused by a picornavirus, comprising administrating a therapeutically and/or preventively effective amount of at least one of the compound of Formula I or a pharmaceutically acceptable salt or hydrate thereof to a patient in need of such treating and/or preventing of the disease associated with an infection caused by a picornavirus.

According to the present invention, the compound of Formula (I) or a pharmaceutically acceptable salt or hydrate thereof is preferably selected from the group consisting of the following compounds:

3-{4-[3-(4-ethoxylphenoxy)propyl]piperazin-1-yl}-6-chloropyridazine,

3-{4-[3-(4-methylphenoxy)propyl]piperazin-1-yl}-6-chloropyridazine,

3-{4-[3-(4-ethylphenoxy)propyl]piperazin-1-yl}-6-chloropyridazine,

3-{4-[3-(4-isopropylphenoxy)propyl]piperazin-1-yl}-6-chloropyridazine,

4-{3-[4-(6-chloropyridazin-3-yl)piperazin-1-yl]propoxy}benzoic acid methyl ester, and 4-{3-[4-(6-chloropyridazin-3-yl)piperazin-1-yl]propoxy}benzoic acid ethyl ester According to the present invention, the compound of the present invention may be prepared as an example by a process of the following reaction scheme:

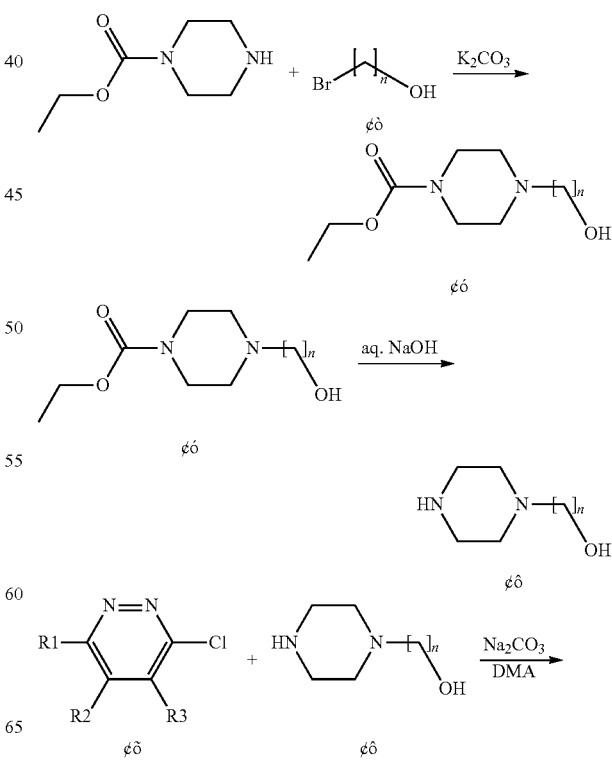

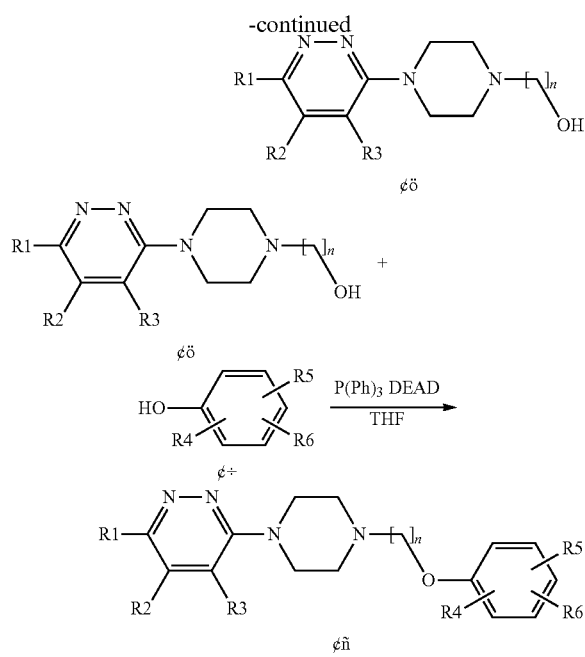

For example, N-piperazine carboxylic acid ethyl ester is reacted with a compound of Formula II in the presence of potassium carbonate in acetonitrile as the solvent at room temperature to generate a compound of Formula III, the compound of Formula III is heated for refluxing in the presence of 10% sodium hydroxide aqueous solution in ethanol as the solvent to generate a compound of Formula IV, a compound of Formula V is reacted with the compound of Formula IV in the presence of sodium carbonate in chloroform, acetone, dichloromethane, N,N-dimethylformamide, N,N-dimethylacetamide (preferably N,N-dimethylacetamide) as the solvents at room temperature to generate a compound of Formula VI, and the compound of Formula VI is reacted with a compound of Formula VII in the presence of triphenylphosphine and diethyl azodicarboxylate in tetrahydrofuran as the solvent at room temperature to generate a compound of Formula I.

According to the present invention, the term "pharmaceutically acceptable salt" of the compound of the present invention comprises acid salts formed with the compound of the present invention and pharmaceutically acceptable inorganic or organic acids, or alkali salts formed with the compound of the present invention and pharmaceutically acceptable alkalis, in which the acid salt include but are not limited to: hydrochloride, hydrobromide, hydroiodide, nitrate, sulfate, bisulfate, phosphate, biphosphate, acetate, propionate, butyrate, oxalate, trimethylacetate, adipates, alginate, lactate, citrate, tartrate, succinate, maleate, fumarate, picrate, aspartate, gluconate, benzoate, mesylate, esylate, besylate, tosilate, and pamoate; and alkali salts include but are not limited to ammonium salt, alkali metal salts such as sodium and potassium salts, alkaline earth metal salts such as calcium and magnesium salts, organic alkali salts such as dicyclohexylamine and N-methyl-D-glucosamine, and amino acid salts such as arginine and lysine salts.

According to the present invention, the pharmaceutical composition of the present invention comprises an effective amount of the compound of Formula (I) of the present invention or a pharmaceutically acceptable salt or hydrate and one or more suitable pharmaceutically acceptable carriers. These pharmaceutically acceptable carriers include but are not limited to: ion exchangers, alumina, aluminum phosphate, lecithin, serum proteins such as human serum protein, buffering substances such as phosphates, glycerol, sorbic acid, potassium sorbate, partial glycerides of saturated vegetable fatty acids, water, salt or electrolyte, such as protamine sulfate, disodium hydrogen phosphate, potassium hydrogen phosphate, zinc salts, colloidal silica, magnesium trisilicate, polyvinylpyrrolidone, cellulose substances, polyethylene glycol, carboxymethylcellulose sodium, polyacrylic esters, beewax, polyethylene-polyoxypropylene block polymer, and lanolin.

The compounds of the present invention are a group of potent inhibitors for a picornavirus, and such compounds are highlighted in the both prevention and treatment of a disease caused by a picornavirus. The disease caused by a picornavirus includes but is not limited to respiratory diseases, hand-foot-mouth diseases, meningitis/encephalitis, acute poliomyelitis, cardiovascular diseases, hemorrhagic conjunctivitis, or hepatitis.

The respiratory diseases include but are not limited to: common cold (such as summer cold), pharyngitis, tonsillitis and croup. These diseases are usually caused by rhinoviruses of the picornavirus family.

According to the present invention, the pharmaceutical composition of the compound of the present invention may be administered via any one of the following manners: oral administration, spray inhalation, rectal administration, nasal administration, bucca administration, vagina administration, topic administration, parenteral administration, such as subcutaneous, intravenous, intramuscular, intraperitoneal, intrathecal, intraventricular, intrasternal, and intracranial injection or infusion, or administration with the help of an explanted reservoir, in which oral, intraperitoneal or intravenous administration is preferred. In addition, in order to allow the compound of the present invention to effectively treat central nervous system disorders, intraventricular administration is preferred to overcome the possible low blood-brain barrier permeability.

For oral administration, the compound of the present invention may be processed in any acceptable forms for oral administration, including but not being limited to tablets, capsules, water solutions or water suspensions. The tablets use a carrier generally comprising lactose and maize starch, additionally comprising a lubrimayt such as magnesium stearate. The capsules use a diluent generally comprising lactose and dry maize starch. The water suspensions usually use a mixture of an active component and suitable emulsifying agent and suspending agent. If necessary, the above oral dosage forms may further comprise some sweetening agents, flavoring agents or coloring agents.

For rectal administration, the compound of the present invention is usually processed to form a suppository, which is prepared by mixing the drug with a suitable unstimulated excipient. This excipient is of solid state, and melts at rectal temperature to release drug. This excipient comprises cocoa butter, bee wax and polypropylene glycol.

For local administration, especially in treatment of neurogenic disease of a readily accessible affected surface or organ such as eye, skin or inferior part of intestinal tract by local external application, the compound of the present invention may be processed into different dosage forms for local administration according to different affected surfaces or organs, which are illustrated as follows:

For local administration to eyes, the compound of the present invention may be processed in a dosage form of micronized suspension or solution, in which the used carrier is isotonic sterile saline with a certain pH, wherein a preservative such as chlorobenzylalkanol salt may be added or not be added. For the eye use, the compound may be processed into ointment form, such as Vaseline ointment.

For local administration to skin, the compound of the present invention may be processed in suitable dosage forms such as ointments, lotions or creams, wherein the active component is suspended or dissolved in one or more carriers. The carriers usable in ointments include but are not limited to: mineral oil, liquid paraffin, white Vaseline, propylene glycol, polyethylene oxide, polypropylene oxide, emulsified wax and water; the carriers usable in lotions or creams comprise but are not limited to: mineral oil, sorbitan monostearate, Tween 60, hexademaye ester wax, hexadecylene aromatic alcohol, 2-octyldodemayol, benzyl alcohol and water.

For local administration to lower intestinal tract, the compound of the present invention may be processed to form the above rectal suppository or suitable enema, and may be processed to form topic transdermal patches.

The compound of the present invention may further be administered in dosage form of sterile injections, including water or oil suspensions for sterile injection, or sterile injection solutions. The usable carriers and solvents include water, Ringer's solution and isotonic sodium chloride solution. In addition, sterile nonvolatile oil may also be used as the solvent or suspending medium, such as monoglyceride or diglyceride.

It is further pointed out that the dose and usage method of the compound of the present invention depend on many factors, including age, body weight, gender, natural health status, nutritional status, activity of compound, administration time, metabolic rate, severity of disease and subjective judgment of diagnostic doctor. The preferred dose used in the present invention is between 0.01 and 100 mg/kg bodyweight/day.

EXEMPLARY MODES FOR CARRYING OUT THE INVENTION

The present invention is further illustrated with the following examples, but the scope of the present invention is not limited to the following examples. Those skilled in the art would understand that the present invention may be changed and modified in many ways without departing from the spirit and scope. The present invention describes in general and/or in details the materials and experimental methods used in experiments. Although many materials and operation methods used for fulfilling the objective of the present invention are well known in the art, they are still described in the present invention in details as much as possible.

As for all of the following examples, standard operations and purification methods known in the art may be used. Unless other stated, all temperatures are represented with ° C. (Celsius degree). The structures of the compounds are determined by nuclear magnetic resonance (NMR) or mass spectrum (MS). Melting point of compound is measured by RY-1 type melting point instrument, thermometer is not calibrated, and m.p. is expressed in ° C. $^1$H NMR is measured by JNM-ECA-400 type nuclear magnetic resonance. Mass spectrum is measured by Agilent 5875 (EI). All solvents used in reactions are subjected to a standard pretreatment, unless specifically indicated otherwise.

Example 1

Synthesis of 3-{4-[3-(4-ethoxylphenoxy)propyl] piperazin-1-yl}-6-chloropyridazine 1.1 Synthesis of 4-(3-hydroxypropyl)piperazinylcarboxylic acid ethyl ester N-piperazine carboxylic acid ethyl ester (25.50 g, 161.39 mmol), 3-bromo-1-propanol (22.43 g, 161.39 mmol), potassium carbonate (55.68 g, 403.48) and anhydrous acetonitrile (200 mL) were placed in a 500 mL round bottom flask, heated for refluxing and stirred overnight. The reaction was cooled down to room temperature, filtered, concentrated and subjected to a column chromatography (eluting agent: dichloromethane/methanol/triethylamine system, v/v/v 100: 1:0.5) to obtain a light yellow oily substance, 26.60 g, yield 76.3%, which was directly used in the next step of reaction.

1.2 Synthesis of 1-(3-hydroxypropyl)piperazine 4-(3-hydroxypropyl)piperazinylcarboxylic acid ethyl ester (14.06 g, 65.09 mmol), 10% sodium hydroxide aqueous solution (150 mL) and ethanol (150 mL) were placed in a 500 mL round bottom flask, heated for refluxing and stirred overnight. The reaction was cooled down to room temperature, distilled under a reduced pressure to remove the solvent to obtain a light yellow oily substance, which was added with 200 mL saturated saline, and the resulting mixture was extracted with dichloromethane (5×200 mL), dried (Na$_2$SO$_4$), filtered, concentrated to obtain a light yellow oily substance, 7.56 g, yield 80.7%, which was directly used in the next step of reaction.

1.3 Synthesis of 3-[4-(6-chloropyridazin-3-yl)piperazin-1-yl]propan-1-ol 3,6-dichloropyridazine (14.90 g, 100 mmol), sodium carbonate (10.60 g, 100 mmol) and DMA (80 mL) were placed in a 250 mL three-necked bottle, and the solution of 1-(3-hydroxypropyl)piperazine (14.4 g, 100 mmol) in DMA (20 mL) was added slowly in dropwise within 30 min under an ice-bath condition. The mixture was stirred at room temperature overnight, distilled under a reduced pressure to remove the solvent to obtain a brown solid, which was subjected to a column chromatography (gradient elution: petroleum/acetone system, v/v 2:1 to acetone) to obtain a white solid, 13 g, yield 50.8%.

1.4 Synthesis of 3-{4-[3-(4-ethoxylphenoxy)propyl] piperazin-1-yl}-6-chloropyridazine 3-[4-(6-chloropyridazin-3-yl)piperazin-1-yl]propan-1-ol (0.77 g, 3 mmol), p-ethoxylphenol (0.41 g, 3 mmol), triphenylphosphine (0.79 g, 3 mmol) and anhydrous THF (20 mL) were placed in a 100 mL three-necked bottle, and DEAD (0.52 g, 3 mmol) was added slowly in dropwise within 10 min under an ice-bath condition. The mixture was stirred at room temperature overnight, subjected to a column chromatography (eluting agent: petroleum/ethyl acetate, v/v 3:2) to obtain a white solid, 0.27 g, yield 23.9%. mp: 125-127° C.; $^1$H-NMR (400 MHz, CDCl$_3$, δ ppm) δ1.39 (t, 3H, J=7.2 Hz), 2.00 (m, 2H), 2.61 (br, 6H), 3.67 (br, 4H), 3.98 (m, 4H), 6.83 (s, 4H), 6.90 (d, 1H, J=9.6 Hz), 7.21 (d, 1H, J=9.6 Hz); EI-MS (m/z): 376.2 [M+H]$^+$.

The following compounds may be prepared by referring to the procedures in step 1.4 of Example 1, replacing p-ethoxyphenol in step 1.4 by different reactants (various substituted phenol).

Example 2

Synthesis of 3-{4-[3-(4-methylphenoxy)propyl]piperazin-1-yl}-6-chloropyridazine

By referring to the procedures in step 1.4 of Example 1, p-methylphenol was used to replace p-ethoxylphenol to obtain the titled compound as a white solid, yield 35.7%. mp: 129-131° C.; $^1$H-NMR (400 MHz, CDCl$_3$, δ ppm) δ2.00 (m, 2H), 2.29 (s, 3H), 2.59 (br, 6H), 3.65 (br, 4H), 4.02 (t, 2H, J=6.0 Hz), 6.81 (d, 2H, J=8.8 Hz), 6.90 (d, 1H, J=9.2 Hz), 7.08 (d, 2H, J=8.4 Hz), 7.21 (d, 2H, J=9.6 Hz); EI-MS (m/z): 346.1 [M+H]$^+$.

Example 3

Synthesis of 3-{4-[3-(4-ethylphenoxy)propyl]piperazin-1-yl}-6-chloropyridazine

By referring to the procedures in step 1.4 of Example 1, p-ethylphenol was used to replace p-ethoxylphenol to obtain the titled compound as white solid, yield 33.3%. mp: 123-125° C.; $^1$H-NMR (400 MHz, CDCl$_3$, δ ppm) δ1.21 (t, 3H, J=7.2 Hz), 2.01 (m, 2H), 2.59 (m, 8H), 3.66 (br, 4H), 4.02 (t, 2H, J=6.0 Hz), 6.83 (d, 2H, J=8.4 Hz), 6.90 (d, 1H, J=9.2 Hz), 7.08 (d, 2H, J=8.4 Hz), 7.21 (d, 2H, J=9.6 Hz); EI-MS (m/z): 360.2 [M+H]$^-$.

Example 4

Synthesis of 3-{4-[3-(4-isopropylphenoxy)propyl] piperazin-1-yl}-6-chloropyridazine By referring to the procedures in step 1.4 of Example 1, p-isopropylphenol was used to replace p-ethoxylphenol to obtain the titled compound as white solid, yield 17.1%. mp: 125-127° C.; $^1$H-NMR (400 MHz, CDCl$_3$, δ ppm) δ1.22 (d, 6H, J=7.2 Hz), 2.01 (br, 2H), 2.60 (br, 6H), 2.86 (m, 1H), 3.66 (br, 4H), 4.03 (t, 2H, J=8.8 Hz), 6.84 (d, 2H, J=8.4 Hz), 6.90 (d, 1H, J=9.2 Hz), 7.14 (d, 2H, J=8.8 Hz), 7.21 (d, 1H, J=9.6 Hz); EI-MS (m/z): 374.2 [M−H]$^+$.

Example 5

Synthesis of 4-{3-[4-(6-chloropyridazin-3-yl)piperazin-1-yl]propoxy} benzoic acid methyl ester By referring to the procedures in step 1.4 of Example 1, p-hydroxybenzoic acid methyl ester was used to replace p-ethoxylphenol to obtain the titled compound as white solid, yield 23.9%. mp: 128-130° C.; $^1$H-NMR (400 MHz, CDCl$_3$, δ ppm) δ2.04 (t, 2H, J=6.4 Hz), 2.60 (br, 6H), 3.66 (br, 4H), 3.89 (s, 3H), 4.11 (t, 2H, J=6.0 Hz), 6.91 (m, 3H), 7.21 (d, 1H, J=9.6 Hz), 7.99 (d, 2H, J=8.8 Hz); EI-MS (m/z): 390.2 [M−H]$^+$.

Example 6

Synthesis of 4-{3-[4-(6-chloropyridazin-3-yl)piperazin-1-yl]propoxy}benzoic acid ethyl ester By referring to the procedures in step 1.4 of Example 1, p-hydroxybenzoic acid ethyl ester was used to replace p-ethoxylphenol to obtain the titled compound as white solid, yield 28.5%. mp: 125-127° C.; $^1$H-NMR (400 MHz, CDCl$_3$, δ ppm) δ1.38 (t, 3H, J=7.2 Hz), 2.05 (br, 2H), 2.61 (br, 6H), 3.66 (br, 4H), 4.11 (t, 2H, J=6.0 Hz), 4.35 (m, 2H), 6.91 (m, 3H), 7.20 (d, 1H, J=9.6 Hz), 7.99 (d, 2H, J=8.8 Hz); EI-MS (m/z): 404.2 [M−H]$^+$.

Experiment Example 1

Activity of Combating Picornavirus in an in Vitro Model

Experimental Materials:

Host cells: HeLa cells (self-stored in the present laboratory)

Virus: rhinovirus 3 (HRV-3) (ATCC: VR-1113)

Positive compounds: see, *Bioorg Med Chem.* 2009, 17: 621-624, the preferred compounds therein, 4-{2-[N-(3-chloropyridazin-4-yl)piperidin-4-yl]ethoxyl}benzoic acid ethyl ester (5f) and 3,6-dichloro-4-{4-[2-(4-ethoxylphenoxy)ethyl] piperazin-1-yl}pyridazine (5c) were separately used as positive control 1 (hereinafter referred to as Control 1) and positive control 2 (hereinafter referred to as Control 2).

1) Determination of the Maximum Nontoxic Dose of the Compound

The drug was dissolved in DMSO, diluted with cell maintenance medium by 20 times, then diluted stepwise by 2 times to form working solutions with different concentrations. HeLa cells were inoculated on 96-well plate in an amount of 10,000 (0.1 mL) per well, added with 0.1 mL maintenance medium, incubated at 37° C. in adherence manner, sucked to remove maintenance medium, replaced it with 0.2 mL of compound working solution, and maintenance medium was used as control. The growth of cell was observed each 24 h, for 3 days. The lowest dilution times which did not cause pathological change was used to determine the nontoxic limit of drug (maximum nontoxic dilution).

2) Prophylactic Administration

Principle: drug was mixed with virus and incubated in advance to block the procedure of viral uncoating and invasion into cell. Method: the drug in a concentration of 100 ng/ml was added to a 12-well plate, then added with a viral dose with TCID$_{50}$ value of about 100, after 0.5 h, 500,000 cells were added to each well, incubated at 33° C., 3 days later, when virus control group showed 100% cytopathic effect (CPE), the effects of drug on preventing cells from phagocytosis were observed, and expressed in cell protection rate (%). The results of prophylactic administration show that various compounds have protection effects in different extents in preventing phagocytosis; in which Control 1, Control 2 and the compounds obtained in various examples all have good protection effects.

3) Therapeutic Administration

The compounds exhibiting better effects in prophylactic administration were further screened for therapeutic administration. 500,000 cells were added to each well, incubated at 33° C. overnight for adherence, then added with a viral dose with TCID$_{50}$ TCID$_{50}$ value of about 100, sucked to remove culture medium after 30 min, drug in a concentration of 100 ng/mL was added to the 12-well plate, the total reaction volume was 2 mL, 48 h later, when the virus control group showed 100% phagocytosis (CPE), the effects of drug on preventing cells from phagocytosis were observed, and expressed in cell protection rate (%).

4) Half Effective Concentration of Compound, Inhibition Index of Compound and Maximum Viral Inhibition Concentration On the basis of primary screening, half effective concentration of compound, inhibition index of compound and maximum viral inhibition concentration were determined.

Measurement of half effective concentration (therapy): 100,000 cells were added to each well of a 24-well plate, incubated at 33° C., then added with virus with 50 μL $TCID_{50}$ value of about 100, compound was diluted by 5 times in gradient manner and added stepwise to the 24-well plate, 48 h later, when virus control group showed 100% phagocytosis (CPE), the concentration of compound that could prevent 50% cells from phagocytosis was determined (expressed in ng/ml). In the meantime, the lowest effective dose of compound was determined.

Measurement of inhibition index of compound: 2 times stepwise dilution was performed from the drug concentration with 100% inhibition effects as determined in the primary screening, and the highest dilution times of drug without showing viral pathology was recorded. The inhibition index of drug was calculated: inhibition index=highest dilution times of viral inhibition/nontoxic limit dilution times.

Maximum viral inhibition concentration: the concentration of compound was set as 100% inhibition of virus titer ($TCID_{50}$ value of about 100), then virus was added stepwise in doubling manner, and the maximum of viral concentration that could be inhibited at the designated compound concentration was determined.

5) Experimental Results

According to the above experimental method, positive controls Control 1, Control 2 and the compounds as prepared in the examples were tested, and their therapeutic activity data were shown in Table 1. The results show that under therapeutic administration condition, Control 1, Control 2 and the compounds as prepared in examples all have good protection effects, and under the same inhibition index condition, some of the compounds of the present invention exhibit activity superior to that of the control compounds.

TABLE 1

Screening data of therapeutic activity of the compounds

| No. | Maximum nontoxic dose (μg/mL) | Cell protection rate (100 ng/mL, $TCID_{50}$ 100) | Half effective concentration (ng/mL) | Inhibition index | Maximum inhibition virus titer $TCID_{50}$ |
| --- | --- | --- | --- | --- | --- |
| Control 1 | 3.9 | 100% | 50 | 1/39 | Not tested |
| Control 2 | 31.3 | 100% | 25 | 1/625 | ≤200 |
| 1 | 7.8 | 100% | <3.2 | 1/625 | >1600 |
| 2 | 7.8 | 100% | 25 | 1/78 | ≤100 |
| 3 | 7.8 | 100% | 25 | 1/156 | ≥800 |
| 4 | 15.6 | 100% | 6.25~12.5 | 1/625 | ≥400 |
| 5 | 7.8 | 100% | 6.25 | 1/625 | ≤400 |
| 6 | 7.8 | 100% | 6.25~12.5 | 1/312 | ≥400 |

What is claimed is:

1. A method for treating a disease or disorder associated with an infection caused by a picornavirus in a subject in need thereof, wherein the disease or disorder is a common cold, which method comprises administrating a compound having Formula Ia

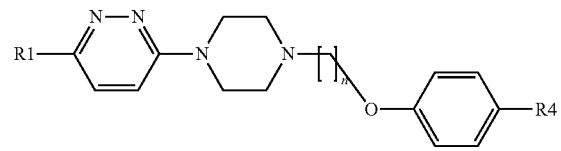

or a pharmaceutically acceptable salt thereof to the subject, wherein
R1 is chlorine;
n is 3 or 4; and
R4 is a straight or branched C1-C6 alkyl,
wherein the picornavirus is a rhinovirus.

2. The method according to claim 1, wherein the compound is selected from the group consisting of
3-{4-[3-(4-methylphenoxy)propyl]piperazin-1-yl}-6-chloropyridazine,
3-{4-[3-(4-ethylphenoxy)propyl]piperazin-1-yl}-6-chloro-pyridazine, and
3-{4-[3-(4-isopropylphenoxy)propyl]piperazin-1-yl}-6-chloropyridazine.

3. A method for treating a disease or disorder associated with an infection caused by a picornavirus in a subject in need thereof, wherein the disease or disorder is a common cold, which method comprises administrating to the subject a pharmaceutical composition comprising:
(a) a compound having Formula Ia

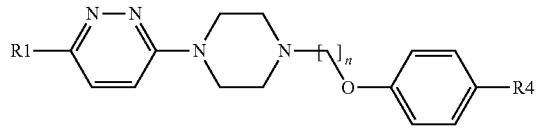

or a pharmaceutically acceptable salt thereof, wherein R1 is chlorine; n is 3 or 4; and R4 is a straight or branched C1-C6 alkyl; and
(b) one or more pharmaceutically acceptable carriers or excipients,
wherein the picornavirus is a rhinovirus.

4. The method according to claim 3, wherein the compound is selected from the group consisting of
3-{4-[3-(4-methylphenoxy)propyl]piperazin-1-yl}-6-chloropyridazine, 3-{4-[3-(4-ethylphenoxy)propyl]piperazin-1-yl}-6-chloro-pyridazine, and 3-{4-[3-(4-isopropylphenoxy)propyl]piperazin-1-yl}-6-chloropyridazine.

5. The method of claim 1, wherein the compound is 3-{4-[3-(4-methylphenoxy)propyl]piperazin-1-yl}-6-chloropyridazine.

6. The method of claim 1, wherein the compound is 3-{4-[3-(4-ethylphenoxy)propyl]piperazin-1-yl}-6-chloropyridazine.

7. The method of claim 1, wherein the compound is 3-{4-[3-(4-isopropylphenoxy)propyl]piperazin-1-yl}-6-chloropyridazine.

8. The method of claim 3, wherein the compound is 3-{4-[3-(4-methylphenoxy)propyl]piperazin-1-yl}-6-chloropyridazine.

9. The method of claim 3, wherein the compound is 3-{4-[3-(4-ethylphenoxy)propyl]piperazin-1-yl}-6-chloropyridazine.

10. The method of claim 3, wherein the compound is 3-{4-[3-(4-isopropylphenoxy)propyl]piperazin-1-yl}-6-chloropyridazine.

\* \* \* \* \*